Fig. 1 Pedigree of 'SYUUGYOKU'

United States Patent [19]

Kanato et al.

[11] Patent Number: Plant 6,726

[45] Date of Patent: Apr. 11, 1989

[54] JAPANESE PEAR TREE

[75] Inventors: Kitsuo Kanato; Yutaka Machida; Itaru Kozaki, all of Ibaraki; Tsutomu Chiba, Chigasaki; Osamu Kishimoto, Utsunomiya; Kanetsugu Seike, Tokyo; Isao Shimura, Fuchu; Kazuo Kotobuji; Mitsuo Omura, both of Ibaraki; Ichiro Kajiura, Shimizu; Yoshihiko Sato; Teruo Kozono, both of Ibaraki, all of Japan

[73] Assignee: Fruit Tree Research Station, Ministry of Agriculture Forestry and Fisheries, Tsukuba, Japan

[21] Appl. No.: 25,892

[22] Filed: Mar. 13, 1987

[51] Int. Cl.[4] ..... A01H 5/03

[52] U.S. Cl. ..... Plt./36

[58] Field of Search ..... Plt./36

[56] References Cited

PUBLICATIONS

Y. Machida et al., Abs. Japan. Soc. Hort. Sci. Autumn Meet., '86, pp. 84–85.

Official Gazette No. 17792 (Jun. 6, 1986), pp. 12–13.

*Primary Examiner*—Robert E. Bagwill

*Attorney, Agent, or Firm*—Armstrong, Nikaido, Marmelstein & Kubovcik

[57] ABSTRACT

Disclosed herein is a Japanese pear tree which has a moderate vigor and an easily maintained moderate spur development, is resistant to black spot disease, and as productive as 'Hōsui'. The tree is cross-incompatible with 'Kōsui' and is assumed to have an $S_4S_5$ genotype, and has brown young leaves and white large flowers which have a pale red color at the pit at fat bud and bloom middle to late in the season and at almost the same time as 'Nijisseiki'. The tree can produce an oblate-shaped fruit which matures early in the season, earlier than 'Nijisseiki', and has a normal keeping quality. The fruit has a large size which is larger than that of 'Nijisseiki', a skin which is covered partly with russet when cultivated without bagging, is at early maturity of the yellowish green color identified in the Munsel® Book of Color as follows:

Hue symbol: 2.5 gy
Chroma: 6
Value: 9, and is at full maturity of the yellow color identified in the Munsel® Book of Color as follows:

Hue symbol: 10 y
Chroma: 6
Value: 9, and a white flesh which is soft, crisp and very juicy, with a high sweetness, a lower acidity, no astringency, and a slight aromatic flavor, giving an excellent dessert quality.

7 Drawing Sheets

BACKGROUND OF THE VARIETY

The present invention relates to a new and distinct variety of Japanese pear tree which has a moderate vigor and an easily maintained moderate spur dvelopment, is resistant to black spot disease *Alternaria alternata* (Fries) Keissler Japanese pear pathotype, and is as productive as 'Hōsui'. The tree is cross-incompatible with 'Kōsui' and is assumed to have an $S_4S_5$ genotype, and has brown young leaves and white large flowers which have a pale red color at the pit at fat bud and bloom middle to late in the season and at almost the same time as 'Nijisseiki'. The tree can produce an oblate-shaped fruit which matures early in the season, earlier than 'Nijisseiki', and has a normal keeping quality. The fruit has a large size which is larger than that of 'Nijisseiki', a yellowish green skin which is partly covered with russet when cultivated without bagging, and a white flesh which is soft, crisp and very juicy, with a high sweetness, a low acidity, no astringency, and a slight aromatic flavor, giving an excellent dessert quality.

The characteristics of cultivars of Japanese pear trees mentioned for comparison are as follows.

'Nijisseiki'; Representative cultivar producing a fruit with yellowish green skin. Middle ripening. The tree is very susceptible to black spot disease. The appearance of the fruit is aesthetically enhanced by bagging.

'Hōsui'; Excellent cultivar known as a "Sansui" (i.e., three cultivars having a Japanese name ending in "sui", respectively, i.e., 'Kōsui', 'Shinsui', and 'Hōsui'). Middle ripening. Bearing a fruit with brown russeted skin.

'Chōjūrō'; Former representative cultivar producing a fruit with brown russeted skin. Middle ripening. The production of this fruit has been recently reduced in Japan.

'Kōzō'; The fruit has a brown russeted skin, and produces a characteristic aroma flavor at full maturation. The tree is little cultivated now in Japan.

'Wase-Kōzō'; Bud mutant of 'Kōzō'. Early ripening. Bearing a fruit with brown russeted skin. This cultivar is little cultivated now in Japan.

The symbol "$S_xS_y$" (wherein x and y are an integer, respectively) used in this specification means the type (genotype) of multiple alleles which controls the incompatibility of plants and is inherent to each cultivar. The relationship between style and pollen, and whether it would be fertile or sterile, depend on the genotype of each. That is, when a style and a pollen both have a same genotype, the relationship becomes sterile. For example, 'Nijisseiki' having an $S_2S_4$ genotype is cross-incompatible with 'Kikusui' having the same genotype $S_2S_4$.

All places and addresses mentioned in this specification are in Japan, unless otherwise specified.

Our breeding program was aimed at obtaining a new early variety of Japanese pear tree producing, first, a fruit having skin which is at early maturity of the yellowish green color identified in the Munsel ® Book of Color as follows:

Hue symbol: 2.5 gy
Chroma: 6
Value: 9, and which is at full maturity of the yellow color identified in the Munsel ® Book of Color as follows:

Hue symbol: 10 y
Chroma: 6
Value: 9, and an excellent quality flesh for dessert; second, resistant to black spot disease; and third, easy to grow and productive.

The new variety of Japanese pear tree was a cross-seedling which originated from a crossing of 'Kikusui (♀)'×'Kōsui (♂)' in 1963 at the Horticultural Research Station of the Ministry of Agriculture and Forestry, residing at Hiratsuka-shi, Kanagawa-ken, Japan, and was top-worked onto 'Chōjūrō' as an interstock and given the number '48-108', in 1966. The tree bore some fruit for the first time in 1969.

The tree was selected in 1971 and subjected to local adaptability tests from 1972 at the experimental stations in main pear growing regions of Japan, e.g., in Tottori-ken, Saitama-ken Ibaraki-ken, Chiba-ken, Miyagi-ken, Fukushima-ken and the like, as the strain number 'Hiratsuka No. 28'. As a result, this new variety of Japanese pear tree according to this invention was judged to be resistant to black spot disease and to produce an excellent quality fruit which is large, has a skin which is at early maturity of the yellowish green color identified in the Munsel ® Book of Color as follows:

Hue symbol: 2.5 gy
Chroma: 6
Value: 9, and which is at full maturity of the yellow color identified in the Munsel ® Book of Color as follows:

Hue symbol: 10 y
Chroma: 6
Value: 9, and can be harvested earlier than 'Nijisseiki'. This new variety of Japanese pear tree was named 'Syuugyoku' in June, 1986.

The pedigree of 'Syuugyoku' is shown in FIG. 1.

'Kikusui', used as a female parent in the breeding of 'Syuugyoku', was selected from seedlings which originated from a crossing of 'Taihaku'×'Nijisseiki' for the purpose of obtaining a variety of Japanese pear tree resistant to black spot disease by Akio Kikuchi at the farm of the former Tokyo Prefectural Horticultural School. The tree was grown and tested at the former Ninoniya Horticulture Division of the Kanagawa Prefectural Agricultural Experiment Station. As a result, the tree was judged to be superior, and named 'Kikusui' in 1927. The main characteristics of 'Kikushi' are as follows.

Tree: Having a good bearing character.
- *Vigor.*—Strong.
- *Spur.*—Bearing heavily.
- *Predominance of axillary flower bud.*—Many.
- *Production.*—Highly productive.
- *Cross-incompatibility.*—Cross-incompatible with, e.g., 'Nijisseiki' and assumed to have an $S_2S_4$ genotype.

Branches:
- *Thickness.*—Medium.

Leaves:
- *Color of young leaves.*—Grayish white.

Flowers:
- *Size.*—Large.
- *Color.*—White.
- *Form of petals.*—Double or semi-double.
- *Pollen.*—Abundant.
- *Flowering time.*—Almost the same time as 'Nijisseiki', e.g., mid-to-late April in Kantō district, Japan.
- *Physiological fruit drop.*—Somewhat much during the harvesting period.

Fruit:
- *Size.*—Medium, about 300 g.
- *Shape.*—Oblate with a very wide and shallow stalk cavity and a slightly wide and deep eye basin.
- *Color of skin.*—Yellowish green.
- *Size of dot.*—Slightly large.
- *Thick peduncle.*—Occurring easily.
- *Flesh.*—Soft and juicy.
- *Taste.*—Having a high sweetness, a slight acidity, and an excellent dessert quality that is better than 'Nijisseiki'.
- *Maturity.*—Ripening at almost the same time as or a little earlier than 'Nijisseiki', e.g., mid-to-late September in the Kantō district, Japan.
- *Keeping quality.*—Somewhat poor.

Resistance to pests and diseases: Resistant to black spot disease and scab.

'Kōsui', used as a male parent in the breeding of 'Syuugyoku', was a seedling of a crossing of 'Kikusui'×'Wase-Kōzō' in 1941 at the Horticultural Research Station of the Ministry of Agriculture and Forestry, residing at Okitsu-machi, Ihara-gun, Shizuoka-ken, Japan, and given the number 'Wi-26'. The tree bore fruit for the first time in 1947. The tree was selected in 1949 and subjected to local adaptability tests at the experimental stations in main pear growing regions of Japan. As a result, the tree was judged to be a superior cultivar that produces fruit with brown russeted skin, and was named 'Kōsui' in 1959. The main characteristics of 'Kōsui' are as follows.

Tree:
- *Vigor.*—Slightly strong.
- *Spur.*—Insufficient bearing, and difficult to maintain.
- *Predominance of axillary flower bud.*—Few.
- *Production.*—Medium.
- *Cross-incompativility.*—Cross-incompatible with, e.g., 'Taihaku', and assumed to have an $S_4S_5$ genotype.

Branches:
- *Thickness.*—Slightly slender.

Leaves:
- *Color of young leaves.*—Reddish brown.

Flowers:
- *Size.*—Large.
- *Color.*—White, but pale red in fat bud.
- *Pollen.*—Abundant.
- *Flowering time.*—Almost the same time as or two to three days later than 'Chōjūrō', e.g., mid-to-late April in Kantō district, Japan.

Fruit:
- *Size.*—Medium, 250-300 g.

*Shape.*—Slightly oblate with a wide stalk cavity and a wide and deep eye basin.

*Color of skin.*—Greenish brown.

*Skin.*—Usually covered with brown spot.

*Thick peduncle.*—None.

*Color of flesh.*—White.

*Flesh.*—Fine, juicy, softer than 'Nijisseiki', and having a firmmess of 3.8 lbs. in Magnessteller's hardness meter index.

*Taste.*—Having a high sweetness (the sugar content of the fruit juice is 12%) and little acidity. Sometimes producing a characteristic aromatic flavor of 'Kōzō' or 'Wase-Kōzō' when the fruit is overripe.

*Maturity.*—Ripening about ten days earlier than 'Chōjūrō', e.g., in the end of August to early September in the Kantō district, Japan.

*Keeping quality.*—Moderate, but good as an early-maturing cultivar.

Resistance to pests and diseases: Resistant to black spot disease and susceptible to canker. The resistance to scab is weaker than that of 'Nijisseiki', but stronger than that of 'Chōjūrō'.

We asexually reproduced this new and distinct variety of Japanese pear tree 'Syuugyoku', by grafting, at the Fruit Tree Research Station, Ministry of Agriculture, Forestry and Fisheries, residing at 2-1 Fujimoto, Yatabe-machi, Tsukuba-gun, Ibaraki-ken, Japan, and confirmed the homogeneity and stability of 'Syuugyoku' according to this invention.

An application for this new variety of Japanese pear tree 'Syuugyoku' under the Seeds and Seedling Law of Japan was filed on Mar. 31, 1986.

SUMMARY OF THE VARIETY

This new variety of Japanese pear tree has a moderate vigor, an easily maintained moderate spur development, a resistance to black spot disease and no sensitivity to pear necrotic spot disease, is as productive as 'Hōsui', is cross-incompatible with 'Kōsui' and is assumed to have an $S_4S_5$ genotype, and has brown young leaves and white large flowers which have a pale red color at the pit at fat bud and bloom middle to late in the season and at almost the same time as 'Nijisseiki'. The tree produces a oblate-shaped fruit maturing early in the season and about two weeks earlier than 'Nijisseiki', and having a large size which is larger than that of 'Nijisseiki', a skin with somewhat large dots which is at early maturity of the yellowish green color identified in the Munsel® Book of Color as follows:

Hue symbol: 2.5 gy
Chroma: 6
Value: 9, and which is at full maturity of the yellow color identified in the Munsel® Book of Color as follows:

Hue symbol: 10 y
Chroma: 6
Value: 9, which is partly covered with more russet when cultivated without bagging than shown by 'Nijisseiki' under the same condition, a white flesh which is soft, crisp and very juicy, with a high sweetness, a low acidity, no astringency, and a slight aromatic flavor, giving an excellent dessert quality, and a normal keeping quality when compared with other cultivars having the same harvesting time as this new variety of Japanese pear tree.

DESCRIPTION OF THE VARIETY

The characteristics of the new and distinct variety of Japanese pear tree 'Syuugyoku' are as follows.

Tree: Having a good bearing character.

*Vigor.*—Medium, not as strong as 'Nijisseiki'.

*Spur.*—Bearing moderately, and easy to maintain.

*Predominance of axillary flower bud.*—Medium.

*Size of leaf bud.*—Medium.

*Time of bud break.*—Late, at the same time as 'Kōsui'.

Figure 1:
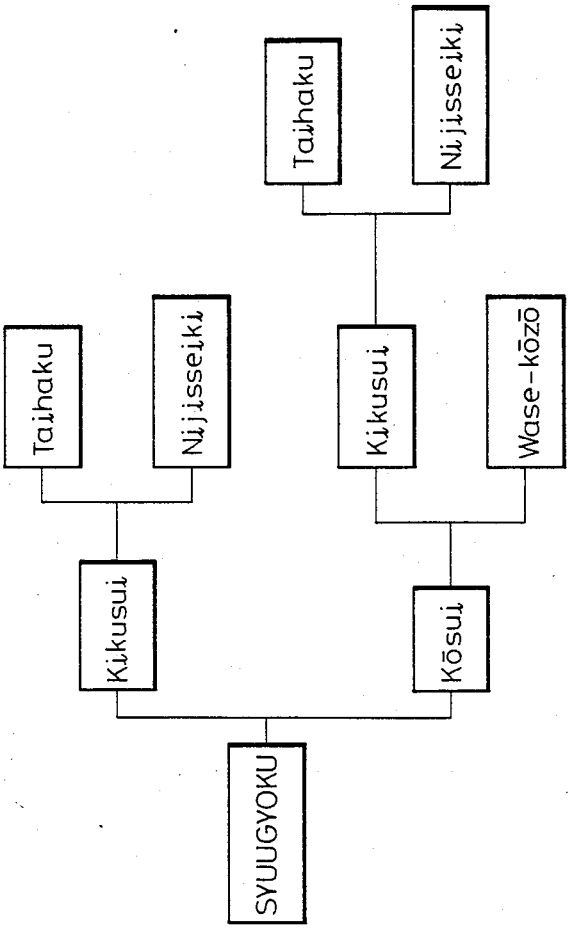
FIG. 1 gives the pedigree of the new and distinct variety of Japanese pear tree 'Syuugyoku'.
Figure 2:
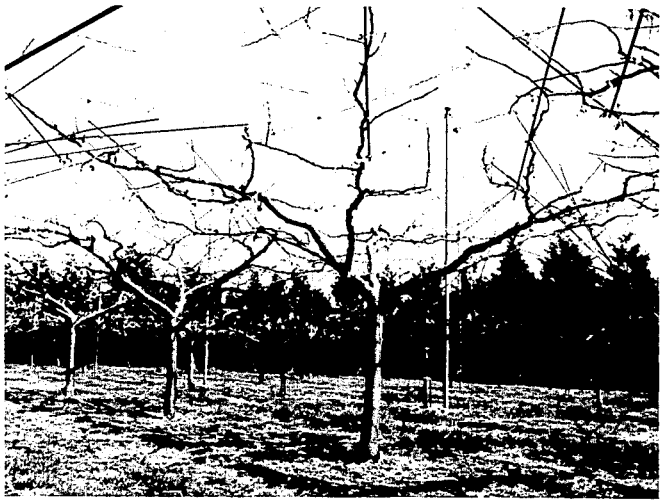
FIG. 2 is a photograph of a shape of the new variety of Japanese pear tree.

*Time of leaf fall.*—Early, at the same time as 'Kōsui' and 'Kikusui'. (see FIG. 2).

*Production.*—As productive as 'Hōshi' and more productive than 'Kōshi', judging from the predominance of flower buds, the size of fruit and the like.

*Cross-incompatibility.*—Cross-incompatible with male parent 'Kōsui', and assumed to have an $S_4S_5$ genotype (i.e., the same genotype of 'Kōsui').

*Cross-compatibiliy.*—Cross-compatible with, e.g., 'Hōshi', 'Chōjūrō', 'Nijisseiki', 'Kikusui' and the like.

Branches:

*Thickness.*—Medium.

*Length of internode.*—Short, 5.5 cm.

*Lenticel.*—Large and long spindle shape, and distributing roughly.

Figure 3:
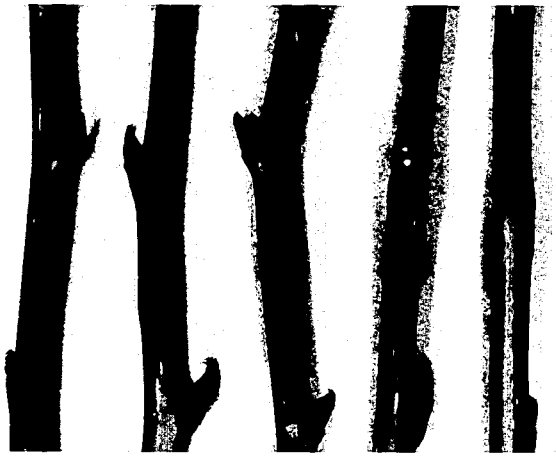
FIG. 3 is a photograph of branches of the new variety of Japanese pear tree.

*Color.*—Dark greenish brown. (see FIG. 3).

Leaves:

*Shape.*—Elliptic, but some oval.

*Size.*—Large.

*Color.*—Green.

Figure 4:
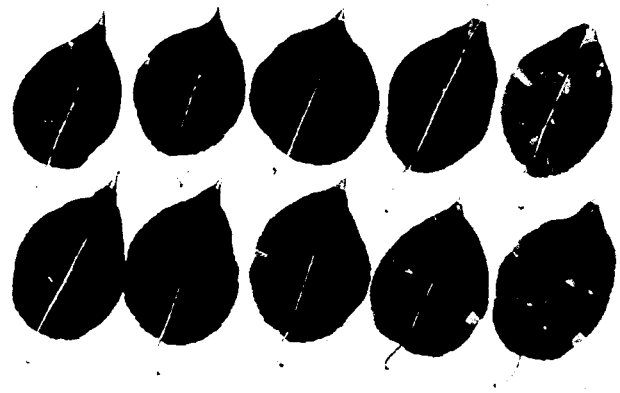
FIG. 4 is a photograph of adult leaves (adaxial) of the new variety of Japanese pear tree.
Figure 5:
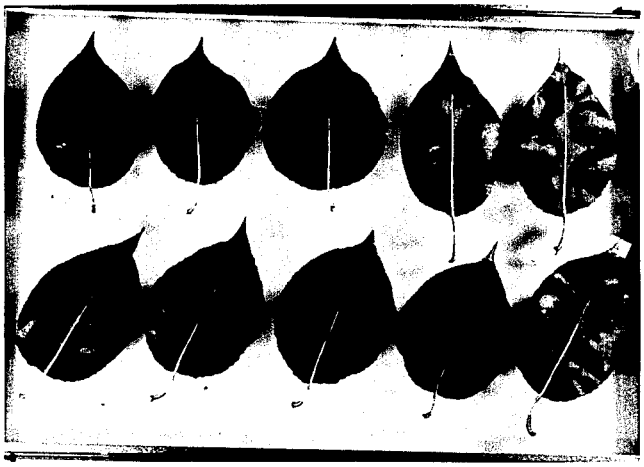
FIG. 5 is a photograph of adult leaves (abaxial) of the new variety of Japanese pear tree.

*Petiole.*—Short. (see FIGS. 4 and 5).

Figure 6:
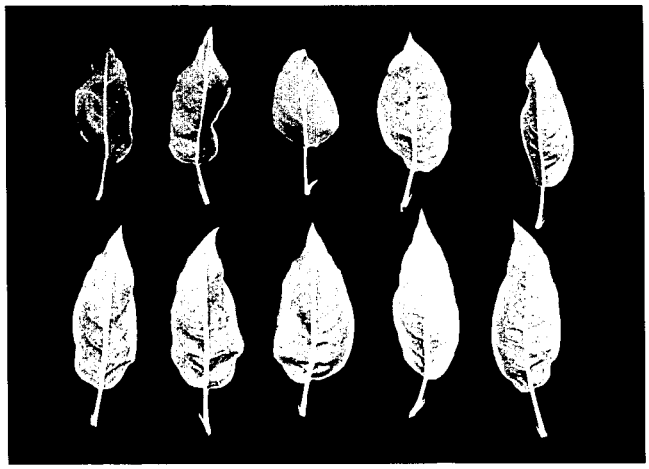
FIG. 6 is a photograph of young leaves (adaxial) of the new variety of Japanese pear tree.
Figure 7:
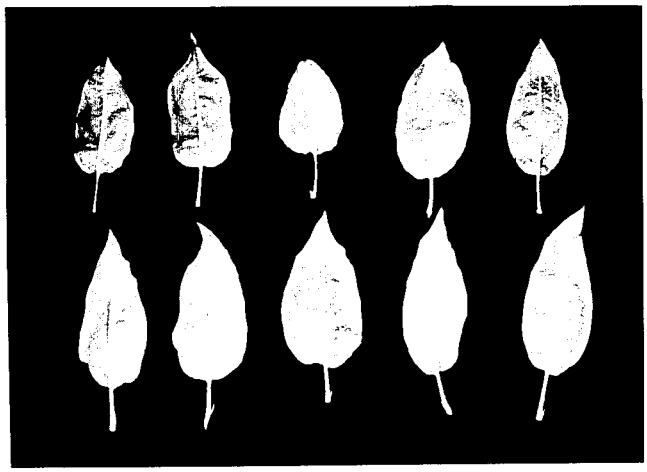
FIG. 7 is a photograph of young leaves (abaxial) of the new variety of Japanese pear tree.

*Young leaves.*—Having a brown color and medium pubescence density. (see FIGS. 6 and 7).

Flowers:

*Size.*—Large, same as 'Kōsui'.

Figure 8:
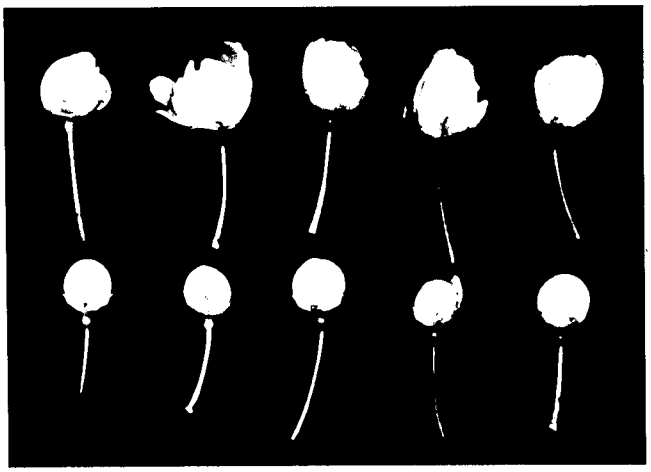
FIG. 8 is a photograph of flower buds of the new variety of Japanese pear tree.
Figure 9:
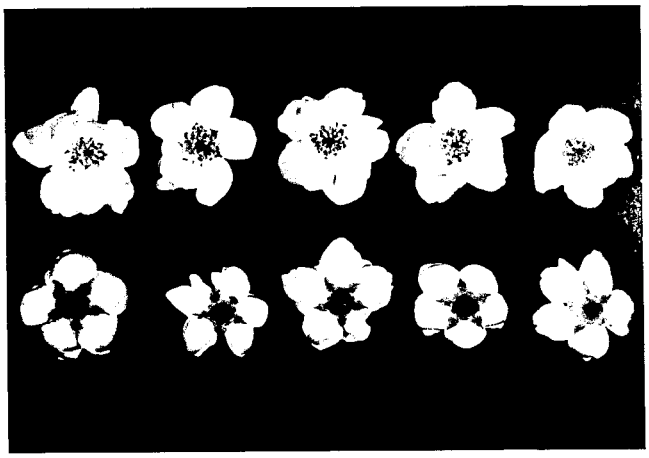
FIG. 9 is a photograph of flowers of the new variety of Japanese pear tree.
Figure 10:
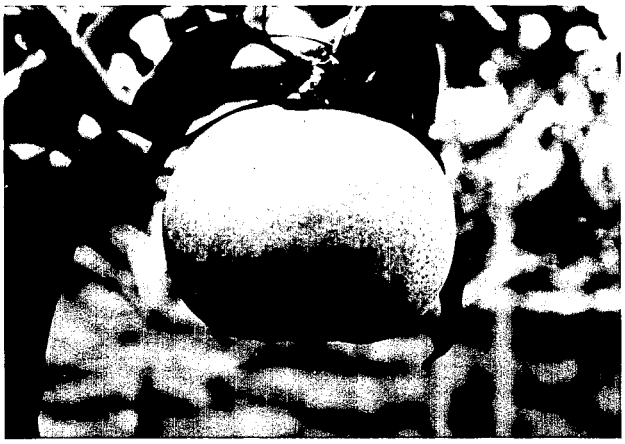
FIG. 10 is a photograph of the new variety of Japanese pear tree in bearing condition.
Figure 11:
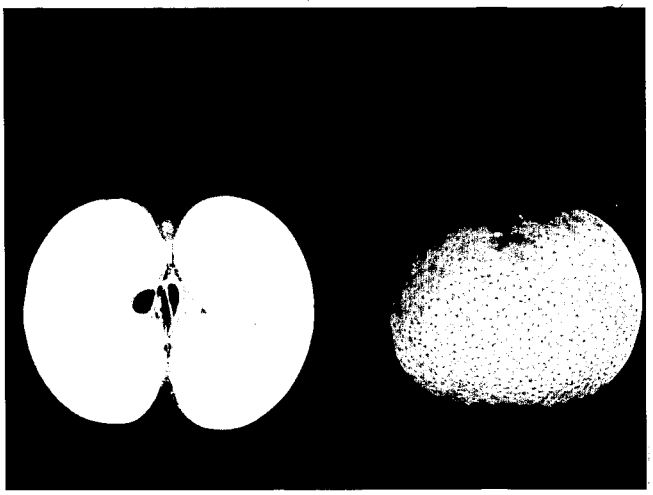
FIG. 11 is a photograph of longitudinal-sectional (left) and side (right) views of fruit of the new variety of Japanese pear tree.
Figure 12:
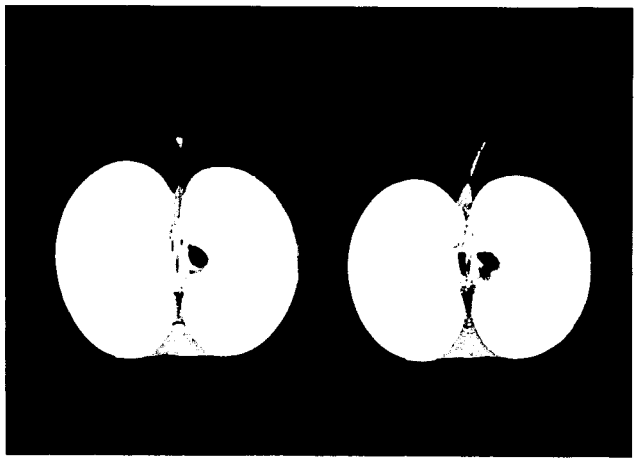
FIG. 12 is a photograph of longitudinal-sectional views of fruit of the new variety of Japanese pear tree; and, FIG. 13 is a photograph of cross-sectional views of fruit of the new variety of Japanese pear tree.
Figure 13:
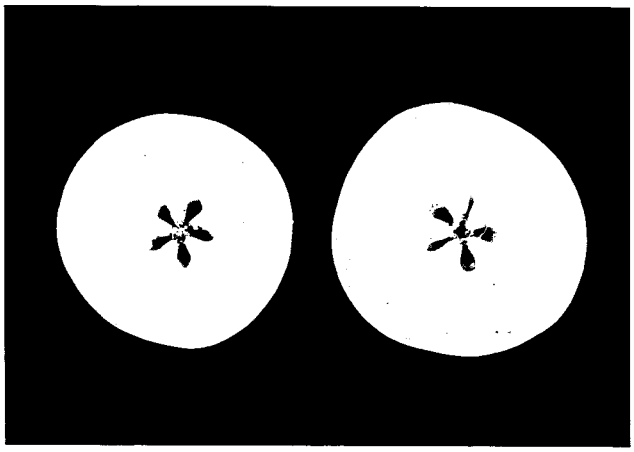

*Color.*—White, but pale red at the pit at fat bud (see FIGS. 8 and 9).

*Shape of petal.*—Large and elliptic.

*Notch of margin of petal.*—Medium.

*Number of petals.*—Many flowers having six or more petals are mixed.

*Color of anther.*—Pale red, paler than 'Kikusui' and 'Kōsui'.

*Pollen.*—Fertile.

*Flowering time.*—Middle to late in the season, almost the same time as 'Nijisseiki', about 1.5 days earlier than 'Kōsui', and two days later than 'Hōsui', e.g., mid-to-late April in the Kantō district, Japan.

Fruit: (see FIGS. 10 to 13).

*Size.*—About 400 g, larger than 'Kōsui', 'Kikusui', and 'Nijisseiki', and almost the same as 'Hōsui'.

*Shape.*—Oblate with a slightly wide stalk cavity of medium depth and a slightly deep eye basin with medium width. The shape of fruit is apt to deviate when the tree is young.

*Calyx perpetual fruit.*—Few.

*Color of skin.*—The skin is at early maturity of the yellowish green color identified in the Munsel ® Book of Color as follows:

Hue symbol: 2.5 gy.

Chroma: 6.

Value: 9.

and is at full maturity of the yellow color identified in the Munsel ® Book of Color as follows:

Hue symbol: 10 y.

Chroma: 6.

Value: 9.

*Size of dot.*—Somewhat large.

*Density of dot.*—Medium.

*Russet.*—More occuring partly, when cultivated without bagging, than shown by 'Nijisseiki' under the same condition.

*Thick peduncle.*—Some.

*Number of locules.*—Many, similar to 'Kōsui'. Many fruit having six to seven locules are mixed.

*Color of flesh.*—White.

*Flesh.*—Fine, crisp, very juicy, and soft. The firmmness is 4.7 lbs. in Magnessteller's hardness meter index, almost the same level as 'Kōsui' and 'Nijisseiki', and higher than 'Hōsui'.

*Taste.*—Having a high sweetness that is almost the same level as 'Kōsui' and 'Hōsui', the sugar content of the fruit juice is about 12% and about 1% higher than 'Nijisseiki', a low acidity that is substantially the same level as 'Kōsui' and less than 'Hōsui' and 'Nijisseiki', the pH of fruit juice is more than or equal to 5.0, no astringency, and a slight aromatic flavor, which give an excellent dessert quality. Judged overall, the fruit quality of 'Syuugyoku' is substantially the same as 'Kōsui' and 'Hōsui'.

*Maturity.*—Ripening early in the season, about two weeks earlier than 'Nijisseiki', and between 'Kōsui' and 'Hōsui', e.g., in late August in Ehime-ken and Ōita-ken, early September in the Kantō district, and late September in Miyagi-ken and Akita-ken, Japan. The fruit growing period is about 138 days, which is 12 days longer than 'Kōsui', 8 days shorter than 'Hōsui', and 14 days shorter than 'Kikusui' and 'Nijisseiki'.

*Use.*—Suitable for dessert.

*Keeping quality.*—Can be kept for 7 to 10 days at 25° C., and therefore normal as a cultivar having the above ripening time. Can be kept longer than 'Hōsui' at 0°–2° C.

Resistance to pests and diseases: Resistant to black spot disease [*Alternaria alternata* (Fries) Keissler Japanese pear pathotype] and non-sensitive to pear necrotic spot. Assumed to be more resistant to canker than 'Kōsui', under observation in the field. Sometimes, physalospora canker occurs.

Core breakdown: None.

Watercore: Occurring rarely, but giving no problems in practice.

Fruit cracking: None.

Culture: The fruit of the new cultivar 'Syuugyoku' is apt to have a russet skin, and it is difficult to produce a fruit having an aesthetically pleasing appearance as 'Nijisseiki' when bagged with a small bag, but a fruit having a considerably improved appearance, compared with one without bagging, can be produced by using a large bag only one time. A fault of this new cultivar is that the yellowish green skin of the fruit has an inferior appearance due to russet, because, with regard to the kind of fruit having a yellowish green skin, the image of 'Nijisseiki' having a beautiful appearance has been a standard until now. However, following the example of the fruit of 'Nijisseiki', which has a russet skin if not bagged, it is necessary to make both sellers and buyers understand that the inferior fruit appearance of this new cultivar is a characteristic of this new variety, but that the inferior appearance in no way affects the excellent dessert quality of the fruit.

It is sometimes difficult to judge the most suitable time for harvesting, as fruit drop occurs at the harvesting time, depending on the year. As a standard, however, the most suitable time for harvesting is that at which the green color fades and a yellow color starts to appear over an area of about 20–40% of the skin of the fruit. On the other hand, the fruit drop can be effectively controlled by using fruit drop control agents. Further, it is possible to reduce the damage caused by the fruit dropping, without harming the fruit quality, by harvesting the fruit three or four days earlier than the harvesting time. The quality of fruit at such an early time is the same as that of fruit at the harvesting time. From the viewpoint of management, this new cultivar is not suitable for growing in a large area, as the harvesting time is comparatively short because of the occurrence of pre-harvest dropping.

Sometimes the fruit hardening disorder occurs depending on soil conditions, e.g., when grown on land where the available depth of soil is shallow and the drainage is bad. However, it seems that the degree of damage caused thereby is less than that of 'Nijisseiki' and 'Chōjūrō.

Normal control methods must be used against scab. To prevent canker, cultivation on land where the ground water table is high, e.g., fields formerly used for rice-growing, should be avoided. Further, proper control methods must be used against physalospora canker, in areas where this disease is prevalent.

From the viewpoint of climate, this new cultivar 'Syuugyoku' can be grown in almost all Japanese pear tree growing areas.

The tree of this new variety 'Syuugyoku' is presently planted and maintained at the Fruit Tree Research Station, Ministry of Agriculture, Forestry and Fisheries, residing at 2-1 Fujimoto, Yatabe-machi, Tsukuba-gun, Ibaraki-ken, Japan.

We claim:

1. A new and distinct variety of Japanese pear tree, substantially as illustrated and described herein, characterized over known Japanese pear trees by (A) having a moderate vigor, an easily maintained moderate spur development, a resistance to black spot disease and no sensitivity to pear necrotic spot disease, (B) being as productive as 'Hōsui', (C) being cross-imcompatible with 'Kōsui' and being assumed to have a $S_4S_5$ genotype, (D) having brown young leaves and white large flowers which have a pale red color at the pit at fat bud and bloom middle to late in the season and at almost the same time as 'Nijisseiki', and (E) producing an oblate-shaped fruit (a) maturing early in the season and about two weeks earlier than 'Nijisseiki' and (b) having (1) a large size which is larger than that of 'Nijisseiki' (2) a skin with somewhat large dots, which is covered partly with more russet when cultivated without bagging than shown by 'Nijisseiki' under the same condition, the color of the skin being at early maturity of the yellowish green color identified in the Munsel ® Book of Color as follows:

Hue symbol: 2.5 gy
Chroma: 6
Value: 9, and at full maturity of the yellow color identified in the Munsel ® Book of Color as follows:

Hue Symbol: 10 y
Chroma: 6
Value: 9, (3) a white flesh which is soft, crisp and very juicy, with a high sweetness, a low acidity, no astringency, and a slight aromatic flavor, giving an excellent dessert quality, and (4) a normal keeping quality when compared with other cultivars having the same harvesting time as this new variety of Japanese pear tree.

* * * * *

UNITED STATES PATENT AND TRADEMARK OFFICE

CERTIFICATE OF CORRECTION

PATENT NO. : Plant 6,726

DATED : April 11, 1989

INVENTOR(S) : Kitsuo KANATO et al

It is certified that error appears in the above-identified patent and that said Letters Patent is hereby corrected as shown below:

On the cover page, Item [75], lines 5 and 6, "Kazuo Kotobuji" should read --Kazuo Kotobuki--.

Signed and Sealed this

Twenty-sixth Day of September, 1989

*Attest:*

DONALD J. QUIGG

*Attesting Officer*

*Commissioner of Patents and Trademarks*